United States Patent
Sauerwald et al.

(10) Patent No.: US 11,927,514 B2
(45) Date of Patent: Mar. 12, 2024

(54) METHOD AND DEVICE FOR CALIBRATING A FLUID DETECTOR HAVING A PRECONCENTRATOR

(71) Applicants: UNIVERSITÄT DES SAARLANDES, Saarbrücken (DE); 3S GMBH, Saarbrücken (DE)

(72) Inventors: Tilman Sauerwald, Saarbrücken (DE); Andreas Schütze, St. Ingbert (DE); Caroline Schultealbert, Saarbrücken (DE); Oliver Brieger, Saarbrücken (DE); Robin Diener, Saarbrücken (DE); Martin Leidinger, Eppelborn (DE); Thorsten Conrad, Bliesransbach (DE); Wolfhard Reimringer, Hemmersdorf (DE)

(73) Assignees: UNIVERSITÄT DES SAARLANDES, Saarbrücken (DE); 3S GMBH, Saarbrücken (DE)

(*) Notice: Subject to any disclaimer, the term of this patent is extended or adjusted under 35 U.S.C. 154(b) by 477 days.

(21) Appl. No.: 17/255,416

(22) PCT Filed: Jun. 14, 2019

(86) PCT No.: PCT/EP2019/065657
§ 371 (c)(1),
(2) Date: Dec. 22, 2020

(87) PCT Pub. No.: WO2019/243182
PCT Pub. Date: Dec. 26, 2019

(65) Prior Publication Data
US 2021/0278327 A1  Sep. 9, 2021

(30) Foreign Application Priority Data
Jun. 22, 2018  (EP) .................................... 18179315

(51) Int. Cl.
*G01N 1/40* (2006.01)
*G01N 33/00* (2006.01)

(52) U.S. Cl.
CPC ......... *G01N 1/405* (2013.01); *G01N 33/0006* (2013.01); *G01N 33/0047* (2013.01)

(58) Field of Classification Search
CPC ........ G01N 1/2214; G01N 1/40; G01N 1/405; G01N 1/2273; G01N 2030/121; G01N 2001/2276; G01N 2001/2217
See application file for complete search history.

(56) References Cited

U.S. PATENT DOCUMENTS

| 4,580,440 A | * | 4/1986 | Reid | ...................... G01V 9/007 73/31.07 |
| 4,909,090 A | * | 3/1990 | McGown | ............. G01N 1/2214 73/864.33 |

(Continued)

FOREIGN PATENT DOCUMENTS

WO  WO-0157515 A2 * 8/2001 ............. G01N 30/00

OTHER PUBLICATIONS

Martin Leidinger et al., Integrated Pre-Concentrator Gas Sensor Microsystem for PPB Level Benzene Detection, Elsevier Sensors and Actuators B 236 (2016) 988-996, www.elsevier.com, Apr. 14, 2016. (10 pages).

(Continued)

*Primary Examiner* — David A. Rogers
(74) *Attorney, Agent, or Firm* — Cook Alex Ltd.

(57) ABSTRACT

A method is provided for calibrating a measurement process for a measurement system having a fluid detector, which is provided with a preconcentrator and a fluid sensor. The measurement system for detecting a concentration of a substance to be detected has a sorption phase, during which the fluid to be detected is enriched for a sorption duration ( (Continued)

$\bar{t}$) in the preconcentrator in a first state, and a measurement phase, in which a concentration of the substance to be detected resulting from the release of the substance to be detected that was enriched in the preconcentrator is measured. The fluid detector is calibrated by adjusting the sorption duration ($\bar{t}$).

9 Claims, 2 Drawing Sheets

(56) References Cited

U.S. PATENT DOCUMENTS

| | | | | |
|---|---|---|---|---|
| 5,083,019 | A * | 1/1992 | Spangler | G01N 27/622 250/282 |
| 5,123,274 | A * | 6/1992 | Carroll | G01N 1/02 73/167 |
| 5,142,143 | A * | 8/1992 | Fite | G01N 33/0049 73/864.81 |
| 5,551,278 | A * | 9/1996 | Rounbehler | G01V 9/007 96/101 |
| 6,354,160 | B1 * | 3/2002 | Staples | G01N 1/2214 73/863.12 |
| 6,378,385 | B1 * | 4/2002 | Bowers | G01N 1/22 73/863.12 |
| 6,588,255 | B2 * | 7/2003 | Pawliszyn | G01N 30/00 422/89 |
| 6,651,520 | B1 * | 11/2003 | Allen | G01N 1/2214 73/863.81 |
| 6,902,701 | B1 | 6/2005 | Hughes et al. | |
| RE38,797 | E * | 9/2005 | Linker | G01N 1/2273 73/863.23 |
| 6,978,657 | B1 * | 12/2005 | Baumann | G01N 1/40 73/31.07 |
| 7,513,171 | B2 * | 4/2009 | Coyle | G01N 1/4022 73/863.22 |
| 7,594,422 | B2 * | 9/2009 | Perry | G01N 1/2214 73/1.02 |
| 8,756,975 | B2 * | 6/2014 | Wu | G01N 1/405 73/864.33 |
| 10,175,198 | B2 * | 1/2019 | Briglin | G01N 1/2273 |
| 10,386,350 | B2 * | 8/2019 | Richter | G01N 33/0036 |
| 11,543,333 | B2 * | 1/2023 | Cho | G01N 1/2247 |
| 2007/0186776 | A1 * | 8/2007 | Yeatman | G01N 1/40 96/4 |
| 2012/0270334 | A1 * | 10/2012 | Ojeda | G01N 1/40 436/178 |

OTHER PUBLICATIONS

Search Report of European priority application EP18179315.9 dated Jan. 17, 2019.
International Preliminary Report of Patentability of PCT/EP2019/065657 dated Dec. 22, 2020.

* cited by examiner

METHOD AND DEVICE FOR CALIBRATING A FLUID DETECTOR HAVING A PRECONCENTRATOR

TECHNICAL FIELD

The present invention relates to fluid detectors for detecting, identifying and quantifying substances to be detected, in particular volatile organic compounds (VOC) in a carrier fluid, such as air, water and the like. In addition, the present invention relates to a method for calibrating a fluid detector having a preconcentrator, in particular comprising a microsystemic arrangement.

TECHNICAL BACKGROUND

Volatile organic compounds are released into the ambient air by artificial materials in various environmental areas. These compounds may accumulate in the air particularly in buildings, and may be harmful to people. Depending on the substance in question, even low concentrations of the substance may affect health and lead to the occurrence of a so called sick building syndrome, for example. Examples of harmful substances are formaldehyde, benzene and naphthalene, which may be relevant even in concentrations in the ppb or sub-ppb range.

In order to monitor the exposure of individuals to volatile organic compounds, fluid detectors may be used that have a sufficient accuracy and selectivity for specific volatile organic compounds.

Various types of gas sensors are known from the prior art, which use in particular sensors the measurement principle of which is based on the use of metal oxide elements, organic semiconductor elements or gas-sensitive field effect transistors as well as sensors based on electrochemical, optical, calorimetric, infrared spectroscopic or gas chromatographic measurement processes. In particular metal oxides, organic semiconductors as well as gas sensitive field effect transistors (gas FET) provide a high sensitivity with respect to volatile organic substances.

However, the selectivity of such detectors is usually poor, so that these sensors are generally not suitable for detecting specific harmful volatile organic substances in air, since many natural volatile organic substances are also already being emitted by living organisms, thereby falsifying the measurement result. Therefore it is usually not possible to use such semiconductor based detectors inside living spaces.

It is generally known to increase the selectivity of gas sensors by combining them with a preconcentrator, which has a good selectivity and is designed to sorb and accumulate only specific volatile organic compounds. The sorbed substances may be desorbed, particularly by heating the preconcentrator, so that the concentration of the specific sorbed substance in the air surrounding the preconcentrator may be increased.

When using a preconcentrator to increase the selectivity of a fluid detector, measurement cycles should include a sorption phase during which the preconcentrator is operated to enrich a particular selected substance, and a measurement phase during which the preconcentrator is activated to release the previously enriched sorbed substance to increase concentration thereof in a carrier fluid above the existing concentration in the environment for measuring by the gas sensor.

For example, U.S. Pat. No. 6,902,701 B1 discloses a fluid detection device, which provides a combination of a preconcentrator for the sorption of specific volatile organic compounds and one or more chemiresistors. The chemiresistors are used to detect—in a measurement phase the volatile organic substances that have been previously enriched during a sorption phase and subsequently released. The preconcentrator and the chemiresistor are arranged in a microsystem chamber, wherein the mass transport of the pre-concentrated volatile organic substances to the chemiresistors occurs by diffusion.

A measurement with such an arrangement requires a definition of the measurement process, particularly the choice of material and volume of the preconcentrator, the durations of the sorption phase and the measurement phase as well as the temperature for the release of the sorbed enriched substance and the like. Furthermore, the measurement results of the fluid sensor depend considerably on characteristics of the immediate environment of the preconcentrator, i.e. the micromechanical structure of the detector, which characteristics may be characterized only inadequately by a physical model.

Therefore, a calibration or adjustment of the fluid detector is necessary in order to assign a specific fluid concentration of a substance to be detected to the electrical measurement value. Such a calibration needs to compensate for the varying characteristics of the measurement path due to manufacturing tolerances and aging effects, particularly with respect to the preconcentrator.

It is basically possible to calibrate the fluid detector for measuring a concentration of the substance to be detected by means of a correction of the evaluation of the fluid sensor signal; however, this is disadvantageous since the lower and upper limits of the measurement range of the concentrations to be detected shift thereby deviating individually for the fluid detectors.

It is therefore an object of the present invention to provide a method and a device for calibrating or adjusting a fluid detector which is provided with a preconcentrator, thereby allowing a higher accuracy of such a fluid detector and a stable measurement range. In addition, a recalibration should be possible in a simple manner.

DETAILED DESCRIPTION OF THE INVENTION

This object is achieved by the method for calibrating a fluid detector which is provided with a preconcentrator and a fluid sensor according to claim 1 and by the device according to the independent claim.

Further configurations are defined in the dependent claims.

According to a first aspect, a method for calibrating a measurement process for a measurement system may comprise a fluid detector, which is provided with a preconcentrator and a fluid sensor, wherein the measurement system for detecting a concentration of a substance to be detected is configured to have a sorption phase, during which the fluid to be detected is enriched for a sorption duration in the preconcentrator in a first state, and a measurement phase, in which a concentration of the substance to be detected resulting from the release of the substance to be detected that was enriched in the preconcentrator is measured, wherein the fluid detector is calibrated by adjusting the sorption duration.

A fluid detector to be calibrated comprises a preconcentrator and a fluid sensor arranged in the proximity thereof for detecting one or more substances to be detected. The preconcentrator is sensitive for one or more substances to be detected and may sorb these substances in a first state and release these substances in a second state in order to increase the concentration of the one or more respective substances in the immediate proximity of the preconcentrator. The sorption on the preconcentrator may be either adsorption, i.e. an adhesion to the surface of a porous material, or absorption in the volume of the preconcentrator material.

One or more of the respective substances enter the range of the fluid sensor by diffusion. The fluid sensor may measure a concentration or a quantity of a substance and provide a corresponding electrical measurement value depending on the concentration of the quantity of the substance. The preconcentrator and the fluid sensor are arranged in a chamber in such a way that a fluid which is in the proximity affects the preconcentrator along a diffusion path, wherein the diffusion of the one or more respective substances to be detected by the fluid sensor is as independent as possible from the concentration of the substances to be detected in the detector proximity.

The operation of such a fluid detector for the measurement of a concentration of the substances to be detected occurs in two phases. In a sorption phase the one or more substances to be detected are enriched in the preconcentrator, and in a measurement phase the enriched substances are released so that they reach the range of the fluid sensor for performing a corresponding measurement of the concentration or quantity of substance thereof. This results in an additional selectivity of the detector, which usually needs to be specified within narrow limits. Depending on the parameters of the cyclic operation of the physical conditions given by the sensor design, the concentration of the one or more substances in the detector environment may be deduced from the electrical measurement value of the fluid sensor.

During the measurement, the fluid sensor provides an electrical which depends on a concentration of the substance to be detected during the measurement phase. The calibration of the fluid sensor, i.e. the sensitivity thereof as a ratio between the measured concentration and the electrical measurement value, is usually factory preset for a number of fluid detectors. The calibration of the fluid detector for measuring a concentration of the substance to be detected by correcting the evaluation of the fluid sensor signal is basically possible; however, this is disadvantageous since the lower and upper limits of the measurement range of the concentrations to be detected shift thereby deviating individually for the fluid detectors provided. Furthermore, this has the disadvantage that the concentration ratio between fluids that are selectively enriched and fluids that are not selectively enriched changes and thus the selectivity of the sensor changes.

Therefore, the above method provides calibration of such a fluid detector by adjusting the duration of enrichment of the substance to be detected in the preconcentrator during the sorption phase.

For characterizing the physical performance of the fluid detector, the mass transport to the preconcentrator and the storage capacity in the preconcentrator may be determined. The duration of enrichment may then be adjusted accordingly so that an electrical measurement value recorded by means of the fluid detectors depends in a defined way on the concentration of the substance to be detected.

Furthermore, the process may include the following steps:
determining a storage capacity of the preconcentrator in a state of equilibrium in the first state;
evaluating the sorption duration as a function of the storage capacity of the preconcentrator and as a function of an indication of a predetermined ratio between stored quantity of substance and concentration of the substance to be detected.

In particular, the following steps may be provided:
determining a quantity of substance stored in the preconcentrator in a non-equilibrium state after a predetermined test duration;
evaluating the sorption duration further depending on the determined quantity of substance.

According to an embodiment, the storage capacity of the preconcentrator may indicate a maximum storable quantity of the substance to be detected for a specific temperature and for a specific concentration of the substance to be detected, and may be determined by a process for determining a quantity of substance stored in the preconcentrator, in particular by a DSC process.

It may be provided that the dynamic sorption of the substance to be detected in the preconcentrator is characterized by a first order differential equation.

According to another aspect, a device for calibrating a measurement process for a measurement system is provided which comprises a fluid detector, which is provided with a preconcentrator and a fluid sensor, wherein the measurement system for detecting a concentration of a substance to be detected is configured to have a sorption phase, during which the fluid to be detected is enriched for a sorption duration in the preconcentrator in a first state, and a measurement phase, in which a concentration of the substance to be detected resulting from the release of the substance to be detected that was enriched in the preconcentrator is measured, wherein the device is configured to calibrate the fluid detector by adjusting the sorption duration.

In accordance with a further aspect, a measurement system is provided comprising a fluid detector having a preconcentrator and a fluid sensor in a chamber opened to the environment through an inlet opening, and a control unit configured to perform a measurement process for detecting a concentration of a substance to be detected with a sorption phase, during which the fluid to be detected is enriched for a sorption duration in the preconcentrator in a first state, and a measurement phase in which a concentration of the substance to be detected resulting from releasing the substance to be detected enriched in the preconcentrator is measured, wherein the control unit is configured to operate the fluid detector by variably adjusting the sorption duration.

BRIEF DESCRIPTION OF THE DRAWINGS

Embodiments are explained in more detail below using the attached drawings, wherein.

DESCRIPTION OF EMBODIMENTS

Figure 1:
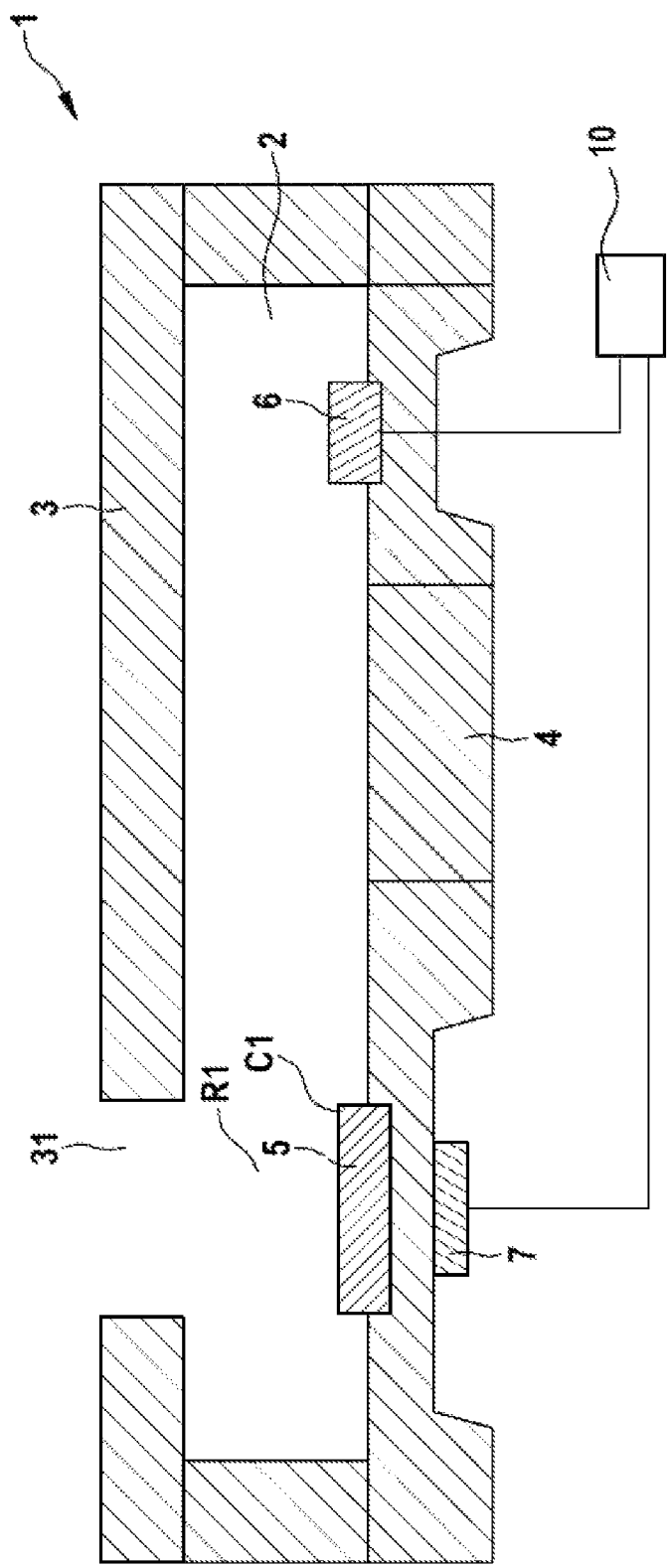
FIG. 1 shows a schematic representation of a fluid detector in a micromechanical design.

FIG. 1 shows a schematic representation of a fluid detector 1 in a micromechanical design. The fluid Detector 1 is used to detect a substance to be detected in a carrier fluid. The fluid detector 1 may be designed as a gas detector, which measures a concentration of so called VOC (volatile organic compounds). Alternatively, the fluid detector may also measure concentrations of fluid substances in a carrier fluid.

The fluid detector 1 comprises a chamber 2, which may be arranged between two flat substrates 3, 4, for example. The substrates 3, 4 may be glass substrates, silicon substrates or in general substrates suitable for micromechanical structuring. One of the substrates 3, which is not further structured apart from an inlet opening, may also be formed from another material, e.g. a metal material.

One of the substrates 4 supports a preconcentrator 5 and an adjacent fluid sensor 6 sensitive to a substance to be detected in chamber 2. The opposite substrate 3 covers the chamber 2, wherein an inlet opening 31 may be provided near the preconcentrator 5, in particular opposite the preconcentrator 5, in order to provide a permeable connection between the ambient fluid and the fluid in chamber 2 of the fluid detector 1.

The preconcentrator 5 is coupled to a heating device 7 in such a way that the preconcentrator 5 may be transferred from a first state, for example a low-temperature state, to a second state, for example a high-temperature state. The heating device 7 may be arranged on the outside of the substrate 4 opposite the preconcentrator 5 in order to supply heat generated by the heating device 7 as quickly and directly as possible to the preconcentrator 5. The heating device 7 serves to transfer the preconcentrator 5 from a first state of a first temperature to a second state of a second temperature. Alternatively, the change of state may also be effected by other means, such as applying an electric or magnetic field or the like.

The preconcentrator 5 may be or may contain a homogeneous material, e.g. a highly viscous fluid, such as PMDS, or a microporous or mesoporous material (e.g. a metal-organic network (MOF)). The material and structure of the preconcentrator 5 may be selected to sorb one or more specific substances to be detected and/or not to sorb one or more specific substances to be excluded from detection.

In the first state, the preconcentrator 5 is capable of sorbing and enriching one or more specific volatile organic compounds to be detected.

The storage capacity of the preconcentrator 5 depends on its temperature. Therefore, due to the reduced storage capacity in the state of equilibrium in the second state (higher temperature), the preconcentrator 5 may release the one or more enriched substances to be detected into the immediate proximity of the preconcentrator 5, i.e. into chamber 2, so that the substance to be detected may diffuse through the—per se immobile (flowless)—fluid in chamber 2 in the direction of the fluid sensor 6.

The fluid sensor 6 may be designed as a semiconducting metal oxide sensor, as an organic semiconductor sensor, as a gas-sensitive FET (gas FET) or similar. Generally, an electrical measurement value, in particular an electrical resistance value, may be determined by use of the fluid sensor 6 as a function of a fluid concentration of the substance to be detected and/or as a function of a quantity of substance (dose) acting on the fluid sensor 6 during a measurement duration window and may be evaluated in a control unit 10.

The heating device 7 for heating up the preconcentrator 5 may be a resistance conductor with a known temperature-dependent resistance, such as made of platinum, so that, in addition to the heating effect by applying electrical power, a temperature measurement may be performed across the electrical resistance of the heating conductor.

The fluid detector 1 is operated in the measurement mode by means of a control unit 10. The control unit 10 controls the fluid detector 1 in a cyclic operation comprising a sorption phase and a measurement phase. In the sorption phase, the substance to be detected passes through the inlet opening 31 to the preconcentrator 5 for a predetermined sorption duration where it is sorbed. The sorption duration is determined as the time between the end of a preceding measurement phase, at which time the preconcentrator 5 is cooled from the second temperature to the first temperature, and the start time of a subsequent measurement phase, from which time the preconcentrator 5 is heated from the first temperature to the second temperature.

By defining the sorption duration of the sorption phase, the quantity of substance stored is determined depending on its concentration in the surrounding fluid. In the measurement phase, a concentration or quantity of substance is measured after a predetermined measurement duration after the end of the sorption phase. Assuming a defined fluid sensor characteristic curve, an evaluable measurement signal is obtained at a constant measurement duration.

Next, the sorption duration is adjusted for calibrating the measurement process using the fluid detector, and is determined for performing the measurement process.

Figure 2:
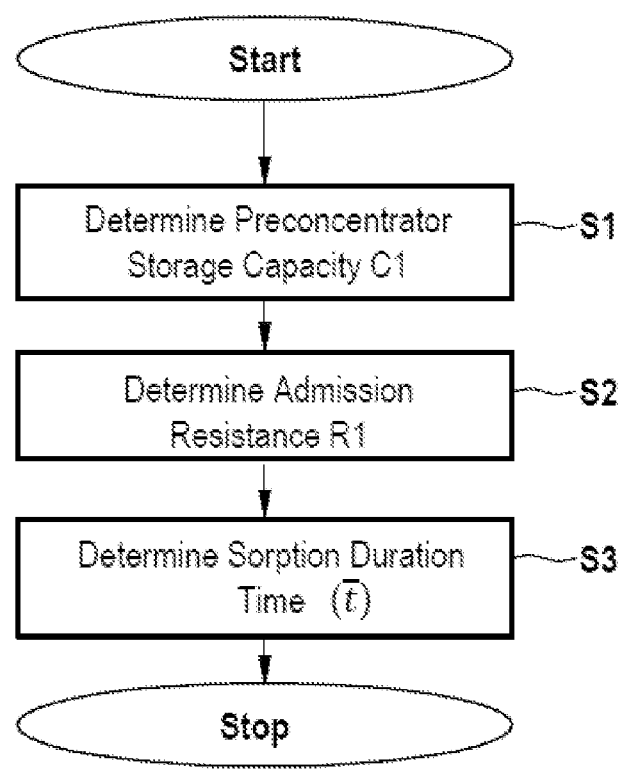
FIG. 2 shows a flow chart illustrating the process for calibrating the fluid detector.

The calibration process is explained in more detail using the flow chart shown in FIG. 2.

The transport of the substance to be detected into and within the fluid Detector 1 is almost completely determined by diffusion due to the smaller dimensions and may therefore be described using Fick's laws. Since the solution of the general case (second Fick's law) is usually not analytically possible and since the results are not illustrative, an acceptable simplification of the description with respect to stationary cases is used. Particularly in the time range of the transition between the sorption and measurement phases, this simplification may not be appropriate. In this case the system may be supplemented by approximations of the general case. For the calibration process it is important that the process is transferred into a stationary state. This may be estimated by the formula:

$$L = \sqrt{Dt}\left(t \geq \frac{L^2}{D}\right)$$

Here, D is the diffusion constant of the gas, L is the characteristic length of the diffusion distance and t is the time until diffusion over a distance L occurs, i.e. the diffusion front has covered the diffusion distance L.

In order to adjust the detector characteristic, i.e. the sensitivity in the form of a ratio between the concentration or quantity of the substance to be detected and the resulting electrical measurement value, the sorption duration is adjusted so that it has a predetermined value of the ratio between the quantity of substance sorbed and the concentration to be measured. This allows a linear dependence of the enriched concentration to be measured by the fluid sensor 6 in the measurement phase on the concentration to be measured.

For this purpose, the storage capacity C1 of the preconcentrator 5 is determined in step S1 by applying a test fluid with a given concentration of one or more substances to be detected. The storage capacity C1 of the preconcentrator 5 corresponds to a quantity of substance n which is sorbed in the preconcentrator 5 at a specific concentration $c_0$ of the test fluid in the stationary case (i.e. at saturation or in a state of equilibrium) at the first temperature. The quantity of substance n stored in preconcentrator 5 is proportional to the sorbed quantity of substance C1 of the substance to be detected.

This quantity of substance $n_{PC}$ may be measured in different ways. The sorbed quantity of substance $n_{PC}$ of the substance to be detected is proportional to the concentration $c_0$ of the substance to be detected, to the distribution coefficient k and to the volume $V_{PC}$ of the preconcentrator 5 in the stationary case according to the formula:

$$n_{PC} = c_0 * k * V_{PC} = c_0 * C1$$

To determine the sorbed quantity n of the substance to be detected in the test fluid, the preconcentrator 5 is adhered with the test fluid of a known concentration until equilibrium is reached. The time assumed for this should be at least 5 $\tau_{med}$ which may be initially estimated with $$\tau_{med} = \frac{1}{R_{1med} * C_{1med}},$$

where $\tau_{med}$, $R_{1med}$, $C_{1med}$ are the median values of the quantities $\tau$, $R_1$, $C_1$. The following applies with respect to the storage capacity:

$$C_1 := k * V_{PC} = \frac{n_{PC}(t \to \infty)}{c_0}$$

For example, the quantity of substance $n_{PC}$ stored in preconcentrator 5 may be determined using a DSC process which is generally known. For this purpose, a heating power of the adhered preconcentrator 5 is measured at a specified temperature ramp. The temperature ramp may be determined by applying a specified electrical power, in particular by specifying a characteristics for the supplied electrical power. The difference of the energy, which is determined on the basis of the integral of the heating power during the measurement duration, is approximately a product of the molar evaporation energy, which is specified for the substance(s) to be detected, and the quantity of substance of the evaporated substance to be detected. The measured heating power may be compensated by means of a reference curve for a heater without preconcentrator 5, wherein the compensated heating power corresponds to the heat capacity of preconcentrator 5. In case of a phase transition of the substance to be detected, the energy for the corresponding phase transition must be taken into account.

Other processes for measuring the stored quantity of substance are also conceivable, e.g. based on an evaluation of a concentration change in the test fluid at a given volume, evaluation of gravimetric changes, mass difference determination of a preconcentrator material sample by means of vibration systems and the like.

To describe the dynamic performance of the fluid detector 1, a description of the mass transport over the diffusion path from the inlet port 31 to the preconcentrator 5 during the sorption phase is necessary. For this purpose, an admission resistance R1 of the substance to be detected to the preconcentrator 5 is determined in step S2. The admission resistance R1 of the substance to be detected through the inlet opening to the preconcentrator 5 is largely determined by the geometric structure of the fluid detector 1. The admission resistance R1 corresponds to a diffusion barrier value and represents a ratio of the diffusion path $x_D$ and the product of the diffusion coefficient D in the carrier medium and a diffusion area A:

$$R1 = \frac{x_D}{D * A}$$

A first-order differential equation is used to determine the temporal change of the quantity of substance in preconcentrator 5 during the sorption phase.

$$c(t) = R_1 \frac{dn_{PC}}{dt} + \frac{n_{PC}}{C_1}$$

The analytically calculated general solution for the differential equation for the quantity of substance in preconcentrator 5 is as follows:

$$n_{PC(t)} = c_0 * k * V_{PC}\left(1 - e^{-\left(\frac{t*D_{air}*A}{x_D*k*V_{PC}}\right)}\right)$$

$$n_{PC(t)} = c_0 * C_1\left(1 - e^{-\left(\frac{t}{R_1*C_1}\right)}\right)$$

Thus, by measuring the quantity of substance $n_{PC}(t_1)$ stored in the preconcentrator 5 after a duration of time $t_1$ after starting to apply a test fluid, the admission resistance R1 may also be determined:

$$R_1 = -\frac{t_1}{C_1 \ln\left(1 - \frac{n_{PC}(t_1)}{c_0 * C_1}\right)}$$

Here, the duration of time should be selected to be $t_1 < 2\tau$.

At this time, the sorption duration $\bar{t}$ to be set is determined in step S3 with known C1 and R1 and with a preset ratio $$\frac{n_{PC}}{c_0}$$

of the quantity of substance $n_{PC}$ and the concentration of the substance $c_0$ to be detected for the fluid detector 1:

$$\bar{t} = -R_1 * C_1 * \ln\left(1 - \frac{\frac{n_{PC}}{c_0}}{C_1}\right)$$

This determination of the sorption duration $\bar{t}$ and its application in a measurement process allows a compensation of manufacturing tolerances and property changes due to aging. In particular, no intervention in the electronic signal evaluation is necessary, so that the entire measurement range may be maintained.

The invention claimed is:

1. A method for calibrating a measurement process for a measurement system for detecting a concentration of a substance to be detected,
    wherein the measurement system comprises a fluid detector comprising:
        a preconcentrator; and
        a fluid sensor,
    wherein the measurement system is configured to have a sorption phase and a measurement phase, being operable by a control unit;
    to enrich the fluid to be detected during the sorption phase for a sorption duration ($\bar{t}$) in the preconcentrator in a first state, and
    to measure a concentration of the substance to be detected resulting from the release of the substance to be detected that was enriched in the preconcentrator, during the measurement phase, the method comprising:
calibrating the fluid detector by adjusting the sorption duration ($\bar{t}$) in the control unit.

2. The method according to claim 1, further comprising the following steps:
determining a storage capacity of the preconcentrator in a state of equilibrium in the first state; and
evaluating the sorption duration ($\bar{t}$) as a function of the storage capacity of the preconcentrator and as a function of an indication of a predetermined ratio between stored quantity of substance and concentration of the substance to be detected.

3. The method according to claim 2, further comprising the following steps:
determining a quantity of substance stored in the preconcentrator in a non-equilibrium state after a predetermined test duration; and
evaluating the sorption duration ($\bar{t}$) further depending on the determined quantity of substance.

4. The method according to claim 1, wherein the storage capacity of the preconcentrator indicates a maximum storable quantity of substance of the substance to be detected for a specific temperature and for a specific concentration of the substance to be detected, and is determined by a process for determining a quantity of substance stored in the preconcentrator, in particular by a DSC process.

5. The method according to claim 1, wherein the dynamic sorption of the substance to be detected in the preconcentrator is specified by a first order differential equation.

6. The method according to claim 1, wherein the measurement process is performed with a sorption phase for the sorption duration (t).

7. The method according to claim 1, wherein the fluid detector is calibrated by adjusting a correction factor and/or a correction offset, wherein the correction factor and/or the correction offset apply an electrical measurement signal of the fluid sensor.

8. A device for calibrating a measurement process for a measurement system for detecting a concentration of a substance to be detected, the device comprising:
a fluid detector, comprising:
which is provided with a preconcentrator; and
a fluid sensor,
wherein the measurement system is configured to have a sorption phase and a measurement phase, being operable by a control unit:
to enrich the fluid to be detected during the sorption phase for a sorption duration ($\bar{t}$) in the preconcentrator in a first state, and
to measure a concentration of the substance to be detected resulting from the release of the substance to be detected that was enriched in the preconcentrator during the measurement phase,
wherein the device is configured to calibrate the fluid detector by adjusting the sorption duration ($\bar{t}$) in the control unit.

9. A measurement system comprising a fluid detector having a preconcentrator and a fluid sensor in a chamber opened to the environment through an inlet opening, and a control unit configured to perform a measurement process for detecting a concentration of a substance to be detected with a sorption phase, during which the fluid to be detected is enriched for a sorption duration ($\bar{t}$) in the preconcentrator in a first state, and a measurement phase in which a concentration of the substance to be detected resulting from releasing the substance to be detected enriched in the preconcentrator is measured, wherein the control unit is configured to operate the fluid detector by variably adjusting the sorption duration ($\bar{t}$).

* * * * *